United States Patent [19]

Sovak et al.

[11] Patent Number: 5,191,119
[45] Date of Patent: Mar. 2, 1993

[54] PROCESS FOR PRODUCING NON-IONIC RADIOGRAPHIC CONTRAST MEDIA UTILIZING N-ALLYLATION

[75] Inventors: Milos Sovak, Rancho Santa Fe; Ramachandran Ranganathan, San Diego, both of Calif.

[73] Assignee: Cook Imaging Corp., Bloomington, Ind.

[21] Appl. No.: 549,256

[22] Filed: Jul. 5, 1990

Related U.S. Application Data

[63] Continuation of Ser. No. 356,268, May 23, 1989, abandoned, which is a continuation of Ser. No. 258,389, Oct. 7, 1988, abandoned, which is a continuation of Ser. No. 676,391, Nov. 15, 1984, abandoned, which is a continuation of Ser. No. 554,308, Oct. 20, 1983, abandoned.

[51] Int. Cl.$^5$ ............................................ C07C 233/65
[52] U.S. Cl. ...................................... 564/153; 560/16; 548/462
[58] Field of Search .................... 560/16; 564/153; 548/45, 52

[56] References Cited

U.S. PATENT DOCUMENTS

| | | | |
|---|---|---|---|
| 3,666,760 | 6/1972 | Ackerman | 560/16 |
| 3,701,771 | 10/1972 | Almen | 424/5 |
| 4,014,986 | 3/1977 | Tilly et al. | 425/5 |
| 4,065,553 | 12/1977 | Tilly et al. | 425/5 |
| 4,065,554 | 12/1977 | Tilly et al. | 425/5 |
| 4,094,966 | 6/1978 | Tilly et al. | 425/5 |
| 4,139,605 | 2/1979 | Felder et al. | 425/5 |
| 4,250,113 | 2/1981 | Wordal et al. | 425/5 |
| 4,348,377 | 9/1982 | Felder et al. | 424/5 |

*Primary Examiner*—Springer: David B.
*Attorney, Agent, or Firm*—Woodward, Emhardt, Naughton, Moriarty & McNett

[57] ABSTRACT

Methods are provided for substituting aromatic carboxylic acids and derivatives thereof and amino substituted aromatic carboxylic acids and derivatives thereof, by forming imides and imide-amides, respectively, by acylation with aliphatic carboxylic acids, substituting at least one nitrogen atom under mild basic conditions with an aliphatic compound having as alkylating agent a displaceable functionality and removing undesired acyl groups, as appropriate.

7 Claims, No Drawings

PROCESS FOR PRODUCING NON-IONIC RADIOGRAPHIC CONTRAST MEDIA UTILIZING N-ALLYLATION

This application is a continuation of U.S. application Ser. No. 356,268, filed May 23, 1989 which is a continuation of U.S. Ser. No. 258,389 filed Oct. 17, 1988; which in turn is a continuation of U.S. application Ser. No. 676,391 filed Nov. 15, 1984; which is a PCT Application based on a priority of U.S. application Ser. No. 544,308 filed Oct. 20, 1983, all of which are now abandoned.

BACKGROUND OF THE INVENTION

1. Field of the Invention

There is a great need for radiographic contrast media which are both non-toxic and economically produced, employing inexpensive and readily available intermediates and reagents. With increasing use of the larger doses demanded by new imaging methods, the incidence of untoward effects caused by ionic contrast media has become a serious concern. Newer, non-ionic radiographic contrast media are less toxic, but their high cost is a substantial deterrent to their generalized use and makes them a major factor in the expense of the diagnostic process. Development of low cost, non-ionic radiographic media has, therefore, become a particularly challenging area of synthetic organic chemistry.

Radiographic contrast media should be water soluble, non-toxic, and have a high iodine content. Most of these non-ionic radiographic contrast media are aromatic amides with one or more amino groups, having polyhydroxy, lower aliphatic alkyl and acyl subgroups bonded to nitrogen, with annular carboxamide and amino groups.

The final synthetic product contains a large number of functionalities in close spatial relationships. An expensive moiety, the triiodinated benzene ring, provides for a major portion of the weight of the product; once the aromatic ring has been iodinated, even small deviations from the theoretical yield can greatly affect the economics of the process. Also contributing to the cost are the water solubilizing functionalities, typically several hydroxyalkylamines, attached as amides. These amines include serinol, 1-amino-2,3-propanediol, N-methyl 1-amino-2,3-propanediol, and aminotetritols; and are all expensive.

In developing improved products it is essential that processes allow for substantial flexibility in the way solubilizing moieties are attached and/or generated on the aromatic ring. In addition, synthesis should provide for high yield, in all steps of the synthetic process.

2. Description of the Prior Art

German OS 2,658,300 describes the preparation of contrast media. See also U.S. Pat. No. 3,701,771 as illustrative of the preparation of contrast media. Also of interest are U.S. Pat. Nos. 4,001,323; 4,021,481 and 4,278,654; as well as UK Pat. Nos. 1,321,591 and 2,031,405; and Dutch application No. 79/05166.

SUMMARY OF THE INVENTION

Procedures for preparing non-ionic radiographic contrast media and novel compounds prepared thereby are provided. The procedures involve at least one of the following steps with a symmetrical triiodobenzamide, where the remaining positions are substituted by a non-oxo-carbonyl group (carboxy carbonyl) or an amino group. The steps: (1) acylation with imide formation and, optionally, peracylation of amino nitrogen; (2) substitution with an olefinically unsaturated compound—alkylation or acryloylation—and subsequent oxidation to a diol; (3) anilide substitution with a 1'-substituted methyloxirane; and (4) alkylation of imide nitrogen with alkyl groups having a reactive leaving group. In addition to the above reactions, additional steps may be involved, which are amide or bis-amide formation with masked hydroxyalkyl amines or diamines, amide formation with ammonia or alkylamines, formation of acyl halides, etc.

The subject invention involves the employment of inexpensive intermediates which can act as polyolamine precursors, particularly olefins, oxiranes, or masked polyols, either substituting at imide or anilide nitrogen or with formation of amides, or the use of acrylic acids as an intermediate to glyceric acids. The resulting products are water soluble, may have low osmolality, low viscosity and low toxicity and can find a variety of uses, particularly as radiographic contrast media with clinically acceptable properties.

DESCRIPTION OF THE SPECIFIC EMBODIMENTS

Synthetic strategies are provided involving individual steps, including individual novel synthetic procedures, to produce substituted nitrogen atoms, where the nitrogen atoms are associated with aroyl amides or amine nitrogen atoms bonded to annular carbon atoms of an aromatic ring, normally a benzene ring. The aromatic rings are highly substituted in that there are no hydrogen atoms. The compounds are mono- or dibenzamides, where the rings are symmetrically triiodinated and the remaining positions are substituted with amino groups to provided phenyl amines having anilino characteristics or carboxamide groups, particularly isophthaldiamide compounds. The synthetic strategies will usually involve minimizing or avoiding the use of polyhydroxyamines, by employing such glycol precursors as olefins and oxiranes. In addition, acylation is used to achieve a variety of purposes, including activation of nitrogen atoms for alkylation, amide nitrogen atoms by imide formation and aniline nitrogen atoms by anilide formation, and as blocking groups to permit selective substitution, particularly alkylation.

Alternative approaches may involve the use of allylamines and amidation with aroyl halides to form amides, which may be subsequently oxidized. Alternatively, nitrogen atoms may be acylated with unsaturated aliphatio acids. e.g., acryloyl acid, followed by oxidation to the diol. A novel method for preparing acyl halides in the presence of the other annular substituents is provided.

The subject compounds will have at least 4 oxy groups, usually at least 5 and may have from 6 to 10 oxy groups as the final monomeric product, with up to 14 oxy groups when dimeric.

The radiographic contrast media and other products may have from one to two aromatic carboxamide groups. The dimeric products will have the carboxamide nitrogen atoms joined by a bond, e.g. hydrazine, or an alkylene group of from 2 to 4 carbon atoms having from 0 to 2 oxy groups, where the remaining valences of the two nitrogen atoms may be satisfied by hydrogen or from 0 to 2, usually 0 to 1, hydroxyalkyl group of from 2 to 4, usually 2 to 3 carbon atoms and from 1 to 3, usually 1 to 2 hydroxyl groups per alkyl group.

Various strategies will be provided for producing the monomeric and dimeric compounds. An important strategy involves the use of imides and anilides for activating nitrogen atoms for alkylation. This strategy may be used by itself or in combination with other strategies, such as acylation with acrylic acid, which may serve as a precursor to glyceric acid and analogs thereof. In some instances, substituted alkyl oxiranes may be employed as precursors to N-polyhydroxyalkyl substituents. In addition, strategies may involve the preparation of acyl halides as intermediates, which will involve preventing undesired side reactions involving other substituents present on the ring. For example, amino groups with benzoyl halides, as distinct from polycarboxylic acid compounds, should be protected by per-substitution. Also, hydroxyl groups should be protected by ether or ester formation.

One synthetic strategy involves the following process for preparing monomeric carboxamides, which process will involve one of the following reaction sequences:

1.   $(H_2N)_n$ $R(CONH_2)_m + AWX \rightarrow ((AW)_2N)_n R(CONHWA)_m$

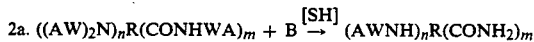

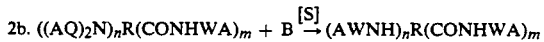

3a.  $(AWNH)_n$ $R(CONH_2)_m + DY + B' \rightarrow (AWN(D))_n R(CONH_2)_m$
3b.  $(AWNH)_n$ $R(CONHWA)_m + DY + B' \rightarrow (AWN(D))_n R(CON(D)WA)_m$
4.   $(AWN(D))_n$ $R(CON(D)WA)_m + B \rightarrow (AWN(D))_n R(CONH(D))_m$ (2a and 3a or 2b and 3b will be employed, while 4 is optional with the b sequence.)

The symbols are defined as follows:

R is a substituted phenyl group with three symmetrically substituted iodine atoms, at least one carboxamide and the remaining two positions substituted with amino, carboxamido or nitrogen substituted derivatives thereof;

n+m equals 3, while m is 1 to 3, preferably 1 to 2 and n is 0 to 2, preferably 1 to 2;

A is an organic group,)which will vary with W and whether it is to be retained or removed, where W is carboxyl, A will be an aliphatic group of from 1 to 4, usually 1 to 3 carbon atoms, preferably 1 to 2 carbon atoms, which may be saturated or unsaturated, usually ethylenic unsaturation, substituted or unsubstituted, particularly oxy substituted, more particularly, protected oxy, such as acyloxy of from 2 to 3 carbon atoms, or alkoxy, including acetals and ketals, with oxo groups of from 1 to 4, usually 1 to 3, carbon atoms; where W is inorganic, A may also be aromatic of from 6 to 10 carbon atoms, unsubstituted or substituted e.g. alkyl, halo, etc.;

W is an acyl functionality, either organic or inorganic, including carbonyl and sulfonyl;

X is a group which activates the carbonyl for substitution on the amide nitrogen and includes halo, normally chloro, an acyl group, which may form a symmetrical or asymmetrical anhydride, e.g., tert.-butyloxycarbonyl, hydroxyl, which may be activated with an appropriate carbodiimide, azido, or the like;

DY is an alkylating agent, where D is a lower aliphatic group of from 1 to 4, usually 1 to 3 carbon atoms, which may be saturated or unsaturated, usually ethylenic, substituted or unsubstituted, particularly oxy substituted, more particularly, protected oxy, such as acyloxy of from 2 to 3 carbon atoms, or alkoxy, including acetals and ketals with oxo groups of from 1 to 4, usually 1 to 3, carbon atoms; and Y is a leaving group which may be displaced by the nitrogen of the imide, and may include halo of atomic number of at least 17, inorganic ester, e.g., sulfate, sulfonate, phosphonate, etc., or the like;

B, B' and B" are basic compounds which will vary with the reactions involved; and S is a non-protic solvent, while SH is a protic solvent, which will vary according to the reactions occurring at substituent sites.

n will be at least 1 in reactions 2b and 3b.

It should be appreciated, that the above list is not exhaustive of the variety of groups which may be used as reactants or of the permissible variation in reactions. Rather, other reaction sequences are permitted as well as other reactants.

For dimeric products the procedure will be similar to monomeric products, but differ in certain details. The carboxylic acid or ester will be acylated and/or alkylated prior to forming the dimeric carboxamide with an activated carboxy group, e.g. an acyl chloride. The reaction sequence will vary as follows, with the same symbols previously indicated having the same meaning:

5. $(H_2N)_{n1} R(CONH_2)_{m1} COG + AWX \rightarrow ((AW)_2N)_{n1} R(CONHWA)_{m1} COG$

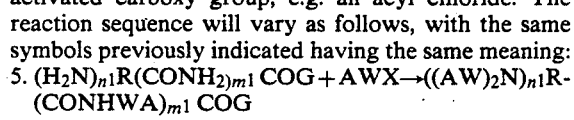

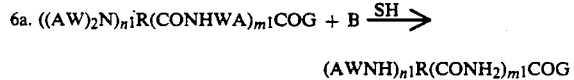

7a.  $(AWNH)_{n1} R(CONH_2)_{m1}$ $COG + DX + B' \rightarrow (AWND)_{n1} R(CONH_2)_{m1} COG$
7b.  $(AWNH)_{n1} R(CONHWA)_{m1}$ $COG + DX + B' \rightarrow (AWN(D))_{n1} R(CON(D)WA)_{m2} COG$
8.   $(AWND)_{n2} R(CON(D)WA)_{m1}$ $COG + ZX \rightarrow (AWND)_{n1} R(CON(D)WA)_{m1} COX$
9.   $(AWND)_{n1} R(CON(D)WA)_{m1} COX + H_p D_q NJND_q H_p \rightarrow ((AWND)_{n1} R(CON(D)WA)_{m1} CON(D^*))_2 Q$
10.  $((AWND)_{n1} R(CON(D)WA)_{m1} CON(D^*))_2 Q + B \rightarrow (AWN(D))_{n1} R(CONH(D))_{m1} CON(D^*))_2 Q$ (6a and 7a or 6b and 7b will employed, while 10 is optional)

The symbols not previously defined are defined as follows:

$n^1 + m^1$ equals 2, while $n^1$ is 1 to 2 and $m^1$ is 0 to 1;

G is an hydroxyl, alkoxyl or oxy salt, e.g. ONa, varying with the conditions of the reaction;

ZX intends a compound capable of activating a carboxyl group, such as an acyl halide, a chlorinating agent, e.g. $PCl_5$ or $SOCl_2$, carbodiimide, etc.;

D* includes hydrogen and the definition for D;

Q is a bond or alkylene group of from 2 to 4 carbon atoms and from 0 to 2 hydroxyl groups;

p+q equals 2, where p is 1 to 2 and q is 0 to 1, and the p's may be the same or different.

The particular reagents will be chosen with regard to their role in the synthetic strategy, as well as their presence or absence in the final product. Where the reagent is to be retained in the final product, the selection will be much more restrictive. Where the reagent has only a transient existence during the synthetic procedure in that it is introduced at one step and removed at a subsequent step, selection, will be less restricted and more directed to the reagents cost and its effect on facilitating the synthesis. Alkylating groups will normally be permanent and while subject to modification, e.g., oxidation, hydrolysis, etc., will be retained with the final product. By way of contrast, acyl groups may or may not be retained in the final product. Where retained in the final product, the acyl group will normally be a carboxyl. Where the acyl group has only a transient presence, it may be either carboxyl or sulfonyl, preferably carboxyl. Usually, sulfonyls will be involved with imide formation rather than amide formation.

A prime function of the subject invention is to have an economic synthesis. Therefore, those reactants or substituents that do not appear in the final product will be selected for low cost and ready availability and for their effect on yield and processing costs. To that extent, certain groups will be preferred over others. For example, for a removable acyl group of an imide, the acetyl or methylsulfonyl groups will be preferred, particularly as acetyl chloride, acetic anhydride or methylsulfonyl chloride. For aliphatic substitution, methyl and ethyl chlorides, bromides or sulfates are preferred as alkylati,ng agents, and 2-propenyl, 2-butenyl and 2-buten-4-hydroxyl (the hydroxyl group is protected) are preferred for intermediates to polyhydroxylated alkyl substituents.

Particular intermediates involved in the subject invention may have the following formula:

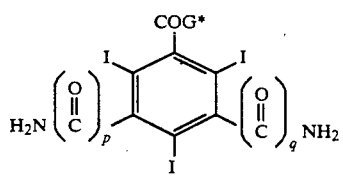  (I)

wherein:
p and q are the same or different and are 0 or 1, preferably p is 0,
while G* is amino, chloro, allylamino, acryloxylamino, aryl of from 2 to 3 carbon atoms, hydroxyl, alkoxy of from 1 to 6 carbon atoms or an oxy salt. The compound of the above formula will be designated as I. For the dimer, G* is other than amino or substituted amino.

Upon acylation of compound I, where G* is amino, the following product will be obtained:

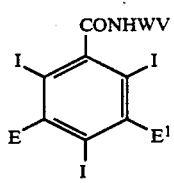  (II)

wherein:
W is CO or SO₂;
V is H, alkyl of from 1 to 6 carbon atoms, particularly 1 to 3 carbon atoms, having 0 to 1 olefinic groups, or aryl of from 6 to 10 carbon atoms, which may be unsubstituted or substituted, e.g. alkyl, halo, etc.

E and E¹ are the same or different and are of the formula:

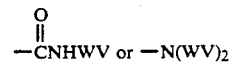

where there is an amino group bonded to an annular carbon atom, the amino group becomes diacylated, while where there is an amide nitrogen, the amide becomes monoacylated.

For the dimer, where G* is not amino, it will come within the definition of G.

Compounds which may serve as starting materials or intermediates may come within the following formula:

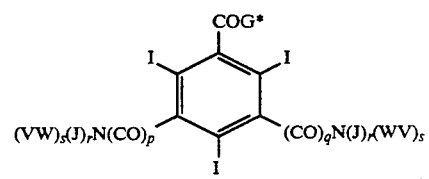

wherein:
G* is amino, allylamino, acryloylamino, acyl of from 2 to 3 carbon atoms, chloro, hydroxyl, alkoxy of from 1 to 6 carbon atoms or an oxy salt;
W is SO₂ or CO;
V is alkyl of from 1 to 3, preferably 1 to 2, carbon atoms having from 0 to 1 site of olefinic unsaturation or from 0 to 1 hydroxy, masked hydroxy, e.g. acetoxy or methoxy, when W is CO, or an organic radical of from 1 to 10 carbon atoms, when W is SO₂;
J is H, (WV), alkyl of from 1 to 2 carbon atoms, allyl, glycidyl or dihydroxypropyl;
p and q are 0 or 1, r is 1 or 2, s is 0 or 1, and p+s and q+s are 1 or 2, where p and/or q are 1, J will usually be other than (VW);
with the proviso that J is other than H when p and q are 0 and G* is chloro.

Usually, there will be only one glycidyl per nitrogen atom. Also, J will usually be other than hydrogen, when the associated symbol p or q is 0, and be hydrogen or alkyl when the associated symbol p or q is 1. Desirably, for an intermediate to polyhydroxylation there will be from I to 3 olefinic or glycidyl groups.

In the preparative procedure, the final product may have G* replaced with G, where G is 1,3- or 2,3-dihydroxy-2, or 1-propylamino or N-methyl derivative thereof or 2,3,4-trihydroxy or 1,3,4-trihydroxy-1 or 2-butylamino.

Final products of interest will have the following formula

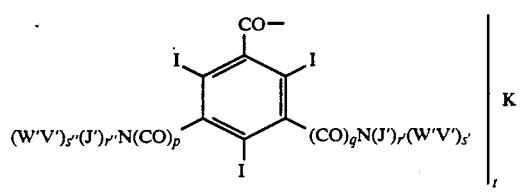

wherein:
t is 1 or 2;

when t is 1, K is amino, alkylamino of from 1 to 2 carbon atoms, or hydroxyalkylamino of from 2 to 4 carbon atoms having from 1 to 3 hydroxyl groups;

when t is 2, K is alkylenediamine of from 2 to 3 carbon atoms or N-polyhydroxyalkyl alkylene diamine; N-polyhydroxyalkyl is of from 3 to 4 carbon atoms and 2 to 3 hydroxyl groups and said alkylene is of from 2 to 3 carbon atoms;

W' is CO;

V' is alkyl of from 1 to 2 carbon atoms, oxyalkyl of from 1 to 3, usually 1 to 2, carbon atoms having from 1 to 3, usually 1 to 2, oxy groups which are hydroxy or methoxy;

J' is H, alkyl of from 1 to 2 carbon atoms, (W'V') or hydroxyalkyl of from 2 to 4 carbon atoms and 1 to 3 hydroxyl groups, where the J' groups may be the same or different;

p, q, s' and s'' are 0 or 1, usually p+s'' and q+s' will be 1; and r' and r'' are 1 or 2.

Usually, J' will be other than W'V' when the associated p or q is 1, usually only one J' per nitrogen being polyhydroxyalkyl.

For the most part, the basic ring structures will be 3,5-diamino-2,4,6-triiodobenzoic acid and 5-amino-2,4,6-triiodoisophthalic acid. The acid groups may be present as the acyl chloride, ester, salt, or amide, in the final product being the amide. In the intermediate compounds amide nitrogens will be substituted with the following groups: which will be removed, acyl sulfonyl; e.g. methylsulfonyl, phenylsulfonyl and toluenesulfonyl; which may or may not be removed, acyl carboxyl, e.g. acetyl, hydroxyacetyl, masked hydroxyacetyl, e.g. methoxyacetyl and acetoxyacetyl, acryloyl, glyceric acid, masked glyceric acid, e.g. acetonide of glyceric acid, 4-hydroxy-2-butenoic acid, masked 4-hydroxy-2-butenoic acid, e.g. 4-acetoxy or 4-methoxy, and 2,3,4-trihydroxybutyric acid and masked derivatives thereof, e.g. acetoxy, methoxy and acetonide; which are not removed, methyl, ethyl, 2-hydroxyethyl, allyl, 1,3 and 2,3-dihydroxypropyl or the diacetoxy or acetonide, glycidyl, 3-hydroxymethylglycidyl or the 3-acetoxy or methoxy, 1,3,4-trihydroxypropyl-2 or acetoxy and/or acetonide thereof, and 2,3,4-trihydroxybutyl or acetoxy and/or acetonide thereof.

Depending upon the conditions, the various acyl groups may be selectively removed. The diacylated annular amino can be selectively transformed to a mono-acylated acylated amino, while retaining the acyl group on the benzamide nitrogen. The mixed benzoyl acyl imide may be hydrolyzed to the benzamide, while retaining monoacyl substituents on the annular amines. This is relevant to the next stage, where selective substitution can be achieved, depending upon the nature of the nitrogen atoms and the substituents. Substitution can occur on the mixed imide and the mono-acylated annular amines, and does not occur under the selected conditions on the diacylated annular amines, nor on the benzamide. One can selectively and stepwise remove acyl groups and introduce nitrogen substituents to provide the desired product. For example, the following illustrative sequences may be performed:

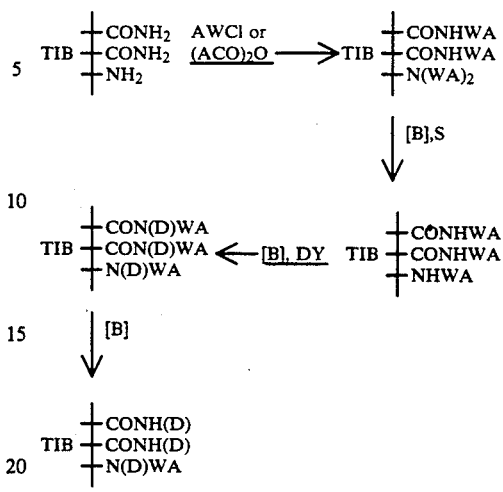

(TIB) intends symmetrical triiodo benzene, with the remaining annular carbons being substituted by the groups set forth. The other symbols which are indicated have been defined previously.

In accordance with the above scheme, one can react all of the nitrogen atoms under mild conditions to produce substituted nitrogen atoms bonded to a saturated aliphatic carbon atom and thus provide for mono-substituted benzoylamides, as well as mono-substituted anilide nitrogen.

A second illustrative procedure is provided as follows:

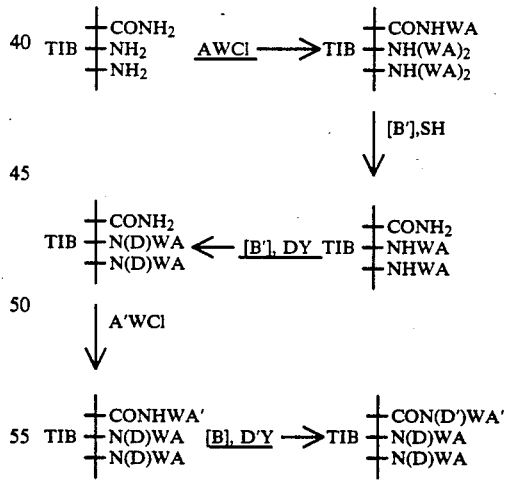

In the above illustration, all of the formulas have been defined except A' and D', which have the same definitions as A and D, respectively, but may differ from A and D, respectively, in the above sequence. Therefore, in accordance with the above sequence, one can provide for different nitrogen substitution on the benzamide nitrogen, as distinct from the anilide nitrogen.

A third illustrative procedure is provided as follows:

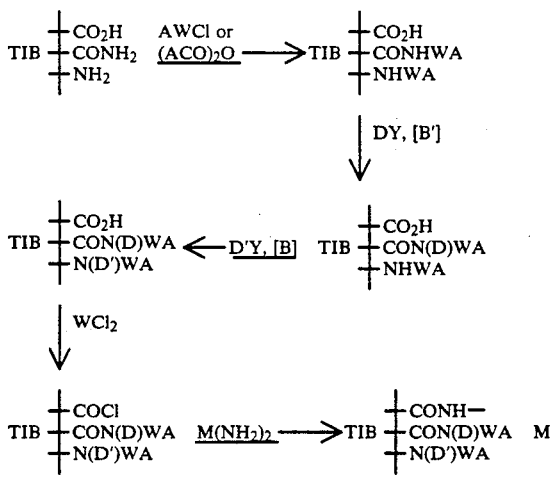

with the symbols as defined previously, except for M which is a bond or alkylene bridge of from 2 to 3 carbon atoms.

The starting materials for the monomeric compounds of the subject invention will be symmetrically substituted triiodo benzamides, having substituents at the 3 and 5 position, which are either carboxamide or amino, where from 0 to 2 of the nitrogen atoms may have aliphatic substituents, usually not more than one substituent, but there will be at least one nitrogen atom which has two hydrogen atoms.

The first step will be the acylation of the ailable nitrogen atoms. The acylation can be for activation of nitrogen for subsequent substitution or protection of nitrogen from subsequent substitution. Thus, the procedure will vary depending upon the desired product. The procedure will also vary depending upon the nature of acylating agent. As indicated previously, the three major types of acylating agents will be acyl halides, particularly acyl chlorides, e.g. carboxyl or sulfonyl, anhydrides, both symmetrical and asymmetrical, and carboxylic acids in combination with a carbodiimide. For acyl halides, acylation will normally occur under mild conditions in an inert polar medium, particularly an amide, e.g., dimethylacetamide or dimethylformamide, at concentrations which may be varied widely, generally being not less than about 0.01M and not more than about 1M, and temperatures in the range of about 0° to 40° C., more usually from about 0° to 30° C. The time will vary depending upon the concentration, the nitrogen being acylated, the temperature, and the like. Normally, the time will be at least about 30 min and not more than about 48 hr, generally being at least about 1 hr and less than about 36 hr. The ratio of the acylating agent may be varied widely, generally being at least stoichiometric, usually in about 1.5 mole excess, and not more than about 10 mole excess, usually not more than 5 mole excess.

For acylation with an anhydride, the anhydride may conveniently serve as a solvent, being in substantial molar excess, usually at least two-fold excess and as high as ten-fold excess or greater. Also included will be a mineral acid, particularly sulfuric acid, which may be present in from about 0.5 to 25 volume percent, more usually from about 1 to 20 volume percent, the volume percent varying depending upon the ratio of the anhydride to the benzamide. Temperatures that will be employed will generally range from 0° to 90° C., more usually from about 10° to 80° C., and times may vary from about 0.1 hr to 6 hr.

The mode of alkylation will vary with the alkylating agent and the desirability of simultaneous removal of acyl groups. Thus, by the conditions employed one can select which nitrogen atoms will be substituted with an aliphatic group. The aliphatic groups will generally be lower alkyl, methyl or ethyl, alkenyl, particularly propenyl or 2-butenyl, or substituted alkyl, particularly oxy substituted alkyl, where the oxy group is protected by an ether or an ester linkage, e.g., oxiranyl, acetonide or acetoxy.

Alkyl halides will normally involve the use of an inert polar solvent, capable of dissolving the benzamide and the alkyl halide and maintaining the compounds in solution at the reaction temperature, which will generally be in the range of about 0° to 40°, more usually in the range of about 10° to 30° C. Particularly convenient as a solvent is dimethyl sulfoxide. A mild base will be employed, a non-hydroxylic base, for example, potassium carbonate, sodium carbonate, or other convenient base, providing a pH in aqueous medium of about 10 to 13, preferably about 11 to 13, or hydroxylic. The amount of base will generally be from about 0.1 to 1 mole ratio to alkylating agent. The time will be at least about 2 hr and not more than about 72 hr, the reaction being monitored to determine whether no further reaction is occurring.

For alkenyl halides the conditions will be substantially the same as for the alkyl halide, except that lower temperatures may be used, generally not exceeding 65° C., usually not exceeding about 60° C., ranging from about 20° to 65° C., more usually from about 30° to 60° C.

With substituted alkyloxiranes, the reaction will be carried out in the presence of base as described for allylation at mildly elevated temperatures, about 35°–100° C., in a hydroxylic solvent, either mono- or dihydroxy, particularly glycols of from 2 to 4 carbon atoms.

Alternatively, the imide salt may be obtained by employing a metal hydride, particularly an alkali metal hydride, e.g., sodium hydride, in at least stoichiometric and preferably excess amounts, usually not greater than about 5M excess in an inert polar solvent, e.g., an N,N-dialkylamide, under mild conditions in conjunction with an aliphatic halide. Single or multiple additions of the hydride and halide may be made. The temperature may generally range from about 20° to 60° C. and periods of time may extend to one week or more. The halide will generally be at least in stoichiometric amount and usually in substantial excess, frequently at least about 2M excess and may be 15M excess or greater.

To enhance activity where a chloride is employed, a small amount of a tetraalkylammonium bromide or iodide salt may be employed, which tends to accelerate the reaction. The amount of the ammonium salt will generally be catalytic, generally ranging from about 1 to 20 mole percent of the halide.

Where monoacylated, the acyl groups may be removed preferentially from imide nitrogen as distinct from anilide nitrogen. A wide variety of conditions may be employed for removing the imide acyl group, including an aqueous or non-aqueous polar organic solvent containing an alkali metal hydroxide of from about 0.1 to 1 Normal, e.g., aqueous dioxane sodium hydroxide; sodium methoxide in methanol, powdered potassium hydroxide in dimethylacetamide, or the like. Temperatures will generally range from about 20° to 50° C. and the base will normally be in excess although in some instances, e.g., methoxide, catalytic amounts may suffice.

In one synthetic strategy, a carboxylic acid or salt is maintained and the amide produced late in the synthetic process. This will be true particularly where one is concerned with dimer formation. In order to form the amide, one will prepare the carboxylic acid chloride, using a carboxylic acid chloride-forming agent, usually an inorganic or organic acid halide. These compounds include thionyl chloride, which is preferred, phosgene, oxalyl chloride, sulfuryl chloride, or the like. The carboxylic acid group may be in the form of the acid, mixed anhydride, or salt. The anilide nitrogens may be persubstituted, having from 1 to 2 acyl substituents or 0 to 1 alkyl substituents depending upon the manner of formation of the acyl halide. Any oxy groups should be protected from reaction with the halogenating agent.

The reaction may be carried out under mild conditions, generally below about 100° C., either in an inert solvent or employing the halogenating agent as the solvent, and using an excess of the halogenating agent, conveniently not more than about a two-fold excess. After completion of the reaction, the acyl halide may be separated from the spent halogenating agent and unreacted halogenating agent by distillation, solvent extraction, or the like and may be used directly without further purification for reaction with an amine to form the amide.

For the dimeric product, the reaction of the acyl halide with the diamine will be carried out in an inert polar organic solvent, e.g., N,N-dialkylated amide, under mild conditions, e.g., room temperature, the reaction allowed to proceed, followed by isolation of the diamide. The product may then be treated substantially in the same manner as the analogous monomeric product, whereby acyl groups may be removed and replaced with alkyl groups, olefins may be oxidized to glycols, and/or substituted alkyl oxiranes may be hydrolyzed and the like.

The workup of the various products at the intermediate stages as well as the final product can employ conventional ways, such as solvent extraction, chromatography, crystallization, or other conventional technique. When hydroxyl groups are present or introduced, the available hydroxyl groups may be derivatized by O-acylation, e.g., O-acetylation, or ketal formation, e.g., acetonide, using acetone or acetone ketal, e.g., methyl or ethyl ketal. The product can usually be isolated in pure form by extraction from the aqueous medium with a substantially water immiscible solvent, chloroform, washing the organic layer and removing the solvent. The product may then be recrystallized from an hydroxylic solvent of low water solubility, e.g., higher alcohol. The O-substituents may be removed by acid hydrolysis, using, for example, an acid ion exchange resin in the crystallization solvent involving alcohol exchange.

The following examples are offered by way of illustration and not by way of limitation:

Experimental

EXAMPLE IA

A. N, N'-bis-allyl 5-amino-2,4,6-triiodoisophthaldiamide (2)

A solution of 5-amino-2,4,6-triiodoisophthaloyl dichloride (1) (45.0 g, 76 mMoles) in 100 ml freshly distilled N,N-dimethylacetamide (DMA) was cooled to 5° C. in an ice bath, and potassium carbonate (21,0 g, 152 mMoles) was added. Allylamine (13.8 g, 242 mMoles) was added over 10 minutes. After most of the heat of the reaction was dissipated, the mixture was removed from the ice batch and stirred overnight at room temperature.

The reaction mixture was poured into an ice water slurry (1:1, 600 ml) with vigorous mechanical stirring. The precipitate was filtered off, washed to neutral pH with water (6×150 ml), and dried at 0.1 mm Hg and 40° C. over KOH pellets to yield a white solid, N,N'-bis-allyl 5-amino-2,4,6-triiodoisophthaldiamide (2), 50.1g (yield 98%).

B. N,N'-bis-allyl 5-acrylamido-2,4,6-triiodoisophthaldiamide (3)

To an ice-cold solution of (2) (42.0 g, 66 mMoles) in 140 ml distilled DMA, was added distilled acryloyl chloride (11.93 g, 132 mMoles) over a ten-minute period. The mixture was removed from the ice bath and stirred at room temperature for 16 hours.

The produce was isolated by pouring the reaction mixture into ice water (1.5 L), with mechanical stirring. The mixture was filtered, the precipitate washed with water (4×200 ml), and dried at 0.1 mm Hg at 45° C. overnight, to produce a white solid, N,N'-bis-allyl 5-acrylamido-2,4,6-triiodoisophthaldiamide (3) (45.0 g, yield 98%).

C. N,N'-bis-(2,3-dihydroxypropyl) 5-glyceramido-2,4,6-triiodoisophthaldiamide (4)

N,N'-bis-allyl 5-acrylamido-2,4,6-triiodoisophthaldiamide (3) (5.0 g, 7.23 mMoles), tetrahydrofuran (25 ml free of stabilizers), water (5 ml), t.-butyl hydroperoxide (70% solution, 5.63 g, 43.4 mMoles), tetraethylammonium acetate tetrahydrate 0.377 g. 1.45 mMoles) and osmium tetroxide (0.018 g, 0.0723 mMoles) were combined in a flask. The mixture was kept at 50° C. in an oil bath for 10 hours.

After cooling in an ice bath, sodium bisulfite (10% solution, 4.8 mMoles) was added and the mixture dried and extracted with 75 methanol/25 tetrahydrofuran. The insoluble salts were filtered off and the solvents removed (4.85 g, 97% yield) to give a brown solid of N,N'-bis-(2,3-dihydroxypropyl) 5-glyceramido-2,4,6-triiodoisophthaldiamide (4), which was further purified by crystallization from octanol/water.

EXAMPLE IB

A. N,N'-bis-allyl 5-(N"-methyl acrylamido)-2,4,6-triiodoisophthaldiamide (5)

N,N'-bis-allyl 5-acrylamido-2,4,6-triiodoisophthaldiamide (3) (Example IA) (20.0 g, 29 mMoles) was added to distilled dimethyl sulfoxide (60 ml). The mixture was warmed to 60° C., allowed to cool to room temperature, and solid potassium carbonate (6.0 g, 43 mMoles) was added. The mixture was cooled to 15° C. in an ice bath, and freshly distilled methyl iodide (7.38 g, 52 mMoles) was added over a ten-minute period.

After 15 hrs stirring at room temperature the solution was poured into ice water (1:2, 500 ml) and the precipitated solid filtered off, washed with water (4×200 ml) and dried in vacuo (0.1 mm Hg) over NaOH pellets at 45° C. to give N,N'-bis-allyl 5-(N''-methyl acrylamido)-2,4,6-triiodoisophthaldiamide (5) (19.0 g, yield 93%).

B. N,N'-bis-(2,3-dihydroxypropyl) 5-(N''-methyl glyceramido)-2,4,6-triiodoisophthaldiamide (6)

In a 1 L flask were combined N,N'-bis-allyl 5-(N''-methyl acrylamido)-2,4,6-triiodoisophthaldiamide (5) (50.0 g, 71 mMoles), acetone (400 ml), water (75 ml), potassium acetate (1.40 g, 14.2 mMoles), t.-butyl hydroperoxide (70%, 46.4 g, 355 mMoles) and osmium tetroxide (0.180 g, 0.71 mMoles, as a solution in 8.27 ml H₂O). The mixture was allowed to stir 22 hours at room temperature.

The reaction mixture was diluted with 500 ml water and extracted with ethyl acetate (3×500 ml).

The aqueous layer was evaporated, redissolved in water, deionized with a mixed bed ion exchange resin (Amberlite), and the water removed to give 51.0 g (95% yield by TLC) of N,N'-bis-(2',3'-dihydroxypropyl) 5-(N''-methyl glyceramido)-2,4,6-triiodoisophthaldiamide (6), which was further recrystallized from n-butanol.

EXAMPLE IC

A. N,N'-bis-allyl 5-(methylamino)-2,4,6-triiodoisophthaldiamide (8)

A solution of 5-(methylamino)-2,4,6-triiodoisophthaldioyl dichloride (7) (130.0 g, 213 mMoles), in 300 ml distilled DMA was cooled in an ice bath to 5° C., and dry potassium carbonate (58.46 g, 426 mMoles) was added. Allylamine (36.5 g, 639 mMoles) was added dropwise over 40 minutes. The reaction mixture was stirred at room temperature overnight.

The product was isolated by pouring the solution into stirred ice water (1:3, 2 L), filtered, and washed with H₂O (3.5–4 L). The product was dried over P₂O₅/0.5 mm Hg/50° C./6 hours to obtain N,N'-bis-allyl 5-(methylamino)-2,4,6-triiodoisophthaldiamide (8) (129.07 g, yield 93%).

B. N,N'-bis-allyl 5-(N''-methyl acrylamido)-2,4,6-triiodoisophthaldiamide (5)

In a 1 L flask were combined N,N'-bis-allyl 5-(methylamino)-2,4,6-triiodoisophthaldiamide (8) (120 g, 184 mMoles) and freshly distilled DMA (350 ml). The solution was cooled in an ice bath, and distilled acryloyl chloride (23.11 g, 255 mMoles) was added over ten minutes. The reaction proceeded for 8 hours at room temperature, when TLC (silica, 95% CHCl₃/5%MeOH) indicated exclusive conversion to a product.

The solution was poured into ice water (1:1, 2 L), with vigorous mechanical stirring, followed by filtration of the precipitated solid, which was washed to neutral pH with water (5×400 ml) and dried in vacuo (0.25 mm Hg) at 50° C. over NaOH pellets to obtain N,N'-bis-allyl 5-(N''-methyl acrylamido)-2,4,6-triiodoisophthaldiamide (5) (122.45 g, 98% yield).

The product was purified by recrystallization from tetrahydrofuran and methanol. One hundred grams of crude solid gave 4 crops of white crystals (yield 85%). By TLC (95 chloroform/5 methanol) Rf (8): 0.77; Rf (5): 0.62. The product is identical to that obtained in Example IB (5).

EXAMPLE ID

A. 5-amino-2,4,6-triiodoisophthaldiamide (9)

To a solution of 5-amino-2,4,6-triiodoisophthaloyl dichloride (1) (15.0 g, 25 mMoles) in 50 ml distilled N,N-dimethylacetamide in a 250 ml Parr pressure bomb was added anhydrous ammonia (3.5 g, 206 mM) in 20 ml DMA and cooled in an ice bath. After 12 hours at 40° C. the excess ammonia was vented and the bomb opened.

The bomb was warmed at 55° C. for 1 hour and the reaction mixture poured into a mechanically-stirred slurry of brine:ice:1N HCl (100 ml:100 g:25 ml). The product was filtered, washed with H₂O (3×50 ml), saturated aqueous sodium bicarbonate (25 ml), H₂O (3×75 ml), and dried overnight at 40° C. in vacuo over potassium hydroxide pellets to yield 5-amino-2,4,6-triiodoisophthaldiamide (9). TLC: (80% CHCl₃/20% MeOH) Rf: (9): 0.51.

B. 5-acrylamido-2,4,6-triiodoisophthaldiamide (10)

A suspension of 5-amino-2,4,6-triiodoisophthaldiamide (9) (20.0 g, 36 mMoles) in DMA (90 ml) was cooled in an ice bath, and distilled acryloyl chloride (6.5 g, 68 mMoles) was added over a three minute period. The reaction proceeded at room temperature for 24 hours, and then was poured into a slurry of ice water (1:3, 650 ml), with mechanical stirring. The precipitate was filtered off, washed to neutral pH with water (100 ml×6), dried in vacuo overnight at 0.1 mm Hg/58° C. over potassium hydroxide pellets, to give 5-acrylamido-2,4,6-triiodoisophthaldiamide (10) (19.20 g, 87.5% yield). TLC: (80% CHCl₃/20% MeOH) Rf (9): 0.51; Rf (10): 0.40.

C. 5-(N-methyl acrylamido)-2,4,6-triiodoisophthaldiamide (11)

A solution of 5-acrylamido-2,4,6-triiodoisophthaldiamide (10) (17.0 g, 28 mMoles) in distilled dimethyl sulfoxide (125 ml) was mixed with potassium carbonate (5.8 g, 42 mMoles) and the mixture cooled,, to 15°–20° C. in an ice bath. Methyl iodide (7.95 g, 56 mMoles) was then added over a three-minute period. The mixture was removed from the ice bath. After 24 hours at ambient temperature, the product was isolated by pouring the reaction mixture into 700 ml ice:brine (1:1). The precipitate was filtered off, washed with water (5×50 ml), and dried in vacuo at 60° C. and 0.3 mm Hg over potassium hydroxide pellets to give 5-(N''-methyl acrylamido)-2,4,6-triiodoisophthaldiamide (11) (15.7 g, 90% yield). TLC: (80% CHCl₃/20% MeOH):Rf (10): 0.52; Rf (11) 0.63.

D. N,N'-bis-acetyl 5-(N''-methyl acrylamido)-2,4,6-triiodoisophthaldiamide (12)

A stirred suspension of 5-(N''-methyl acrylamido)-2,4,6-triiodoisophthaldiamide (11) (6.25 g, 10 mMoles) in acetic anhydride (18 ml, 190 mMoles) was cooled in an ice bath. Concentrated sulfuric acid (2 ml) was added dropwise over a three minute period. After 6 hours at room temperature, the solution was poured into a slurry of ice/brine (1:1, 400 ml). The precipitate was filtered off, washed with water (5×30 ml) to neutral pH and dried for 10 hours at 25° C. and 0.3 mm Hg over potassium hydroxide pellets to give N,N'-bis-acetyl 5-(N''-methyl acrylamido)-2,4,6-triiodoisophthaldiamide (12)

in nearly quantitative yield. TLC: (85% CHCl₃/15% MeOH) Rf (11): 0.54; Rf (12): 0.70.

E. N,N'-bis-acetyl, N,N'-bis-allyl 5-(N"-methyl acrylamido)-2,4,6-triiodoisophthaldiamide (13)

N,N'-bis-acetyl 5-(N"-methyl acrylamido)-2,4,6-triiodoisophthaldiamide (12) (2.13 g, 3 mMoles) was placed in a flask and distilled dimethyl sulfoxide (6 ml) was added, with stirring. Potassium carbonate (1.04 g, 7.5 mMoles) was added to a homogenized solution followed by distilled allyl chloride (0.918 g, 12 mMoles) over a one minute period.

After 8 hours at 45° C., the product was isolated by pouring the mixture into a stirred slurry of ice:brine1N HCl (10 g:20 ml:10 ml). The precipitate was filtered off, washed with water (6×10 ml) to neutral pH and dried overnight at ambient temperature and 0.4 mm Hg over $P_2O_5$. This gave N,N'-bis-acetyl, N,N'-bis-allyl 5-(N"-methyl acrylamido)-2,4,6,-triiodoisophthaldiamide (13) (2.05 g, 87% yield). TLC: (90% CHCl₃:10% MeOH, Rf: 0.87).

F. N,N'-bis-allyl 5-(N"-methyl acrylamido)-2,4,6-triiodoisophthaldiamide (5)

A solution of 0.8 g N,N'-bis-acetyl, N,N'-bis-allyl 5-(N"-methyl acrylamido)-2,4,6-triiodoisophthaldiamide (13) (1.01 mMoles) in 5 ml dioxane and 5 ml 0.5N sodium hydroxide was heated at 40° C. for 2 hours in an oil bath.

The product was isolated by pouring the reaction mixture into an ice-brine slurry (1:1, 20 ml), followed by filtration. The solid was washed with water (6×5 ml) and dried at 4 mm Hg and 62° C. for 60 hours to give N,N'-bis-allyl 5-(N"-methyl acrylamido)-2,4,6-triiodoisophthaldiamide (5) (655 mg, 92% yield).

This product is the same as in Examples IB (5) and IC (5).

EXAMPLE IIA

A. N,N'-bis-acetyl 5-diacetylamino-2,4,6-triiodoisophthaldiamide (14)

To a cooled, stirred suspension of 5-amino-2,4,6-triiodoisophthaldiamide (9) (20 g, 0.036 mole) in acetic anhydride (120 ml), conc. $H_2SO_4$ (7 ml) was added over 20 min. After 6 hours at 50° C. the reaction mixture was poured into ice cold water (900 ml), filtered, washed with water (500 ml), 10% bicarbonate solution, and water, triturated with toluene, the solvent removed, and the solid dried under vacuum at 44° C. The product contained 85% of N,N'-bis-acetyl 5-diacetylamino-2,4,6-triiodoisophthaldiamide (14). The product was employed in the next step without purification.

B. N,N'-bis-allyl 5-(N"-allyl N"-acetyl amino)-2,4,6-triiodoisophthaldiamide (15)

To a stirred solution of crude (14) (2.69 g, 3.72 mMole) in DMA (13 ml), powdered potassium hydroxide (0.937 g, 16.73 mMole) was added and the contents stirred at 40° C. for 4 hours.

Sodium bicarbonate (0.336 g, 4 mMole), potassium carbonate (0.75 g, 5.56 mMole) and allyl chloride (1.8 ml, 22.2 mMole) were added under stirring at 40° C. for 6 hours. The acetimides were hydrolyzed off in situ with 1N sodium hydroxide (9.5 ml) and water (5 ml) at 50° C. in 1.5 hr. The reaction mixture from which the product had partly precipitated out was poured into ice cold water, the solid filtered, washed and dried (yield 1.82 g, ca70% isolated yield; 90% yield by TLC). N,N'-bis-allyl 5-(N"-allyl, N"-acetyl amino)-2,4,6-triiodoisophthaldiamide (15) was crystallized from acetone-hexane as colorless needles.

C. N,N'-bis-(2',3'-dihydroxypropyl) 5-(N"-2",3"-dihydroxypropyl, N"-acetyl amino)-2,4,6-triiodoisophthaldiamide (16) (Iohexol)

To a cooled, stirred suspension of (15) (2 g, 2.78 mMole) in acetone (10 ml) were added aqueous tetraethylammonium acetate (0.125 g, 0.55 mMole), 70% aqueous t.-butyl hydrogen peroxide (1.6 ml, 12.5 mMole), and aqueous osmium tetroxide (0.007 g, 0.028 mMole). The reaction mixture was kept in an oil bath for 3 hours at 45°–48° C. and then at room temperature for 6 hours. Excess peroxide was removed from the reaction mixture with 10% aqueous sodium sulphite solution (10 ml); after adjusting the pH to 6.5 with diluted HCl, the solution was evaporated to dryness in vacuo. The product was dissolved in water (30 ml), adsorbed on Diaion resin and eluted with water, then with a water-methanol mixture. From water and methanol-water (10%) eluents, N,N'-bis-(2',3'-dihydroxypropyl) 5-(N"-2,3-dihydroxypropyl N"-acetyl amino)-2,4,6-triiodoisophthaldiamide (16) was obtained (1.80 g, 85% yield) as a white powder.

Comparison of (16) with Iohexol (Nyegaard Co.) showed it to be identical by HPLC (aminopropyl silica, 90 acetonitrile/10 $H_2O$).

EXAMPLE IIB

A. N,N'-bis-(2',3'-dihydroxypropyl) 5-(N"-2",3"-dihydroxypropyl, N"-acetyl amino)-2,4,6-triiodoisophthaldiamide (16)

N,N'-bis-(2',3'-dihydroxypropyl) 5-acetylamino-2,4,6-triiodoisophthalamide (17) prepared as described in U.S. Pat. No. 4,250,113 (375 mg, 0.5 mMole) was heated at 85° C. with sodium bicarbonate (84 mg, 1.0 mMole) and epichlorohydrin (2 ml, 26.6 mMole) in 1,2-propanediol (4 ml) and a trace of water for 60 min to give N,N'-bis-(2',3'-dihydroxypropyl) 5"-(N"-2",3"-dihydroxypropyl, N"-acetyl amino)-2,4,6-triiodoisophthaldiamide (16) (Example IIA) in 95% yield. TLC: CHCl₃ : MeOH 6:4, HPLC: 90 acetonitrile:10 water, 2 ml/min, NH₂ propyl 0.5×25, 10μ Alltech column.

EXAMPLE IIIA

A. 3,5-diaminobenzamide bis-hydrochloride (19)

3,5-dinitrobenzamide (18) (412.0 g, 2.00 moles, Aldrich) was added to a suspension of 10% Pd/C (10.4 g) in concentrated HCl (360 ml) and water (3.64 L). The mixture was hydrogenated at 60psi in a Parr hydrogenation apparatus until hydrogen was no longer being consumed. The solution was filtered through a Celite pack and washed with 500 ml water. The filtrate and washings of 3,5-diaminobenzamide bis-hydrochloride (19), were combined and used for the subsequent iodination.

B. 3,5-diamino-2,4,6-triiodobenzamide (20)

The 3,5-diaminobenzamide bis-hydrochloride (19) was diluted with water to 20.0 L, stirred and, over a twenty minute period, 3.2 equivalents of $KICl_2$ (4.12 L of 1.55M $KICl_2$) were added.

After 15 minutes, the mixture was filtered, washed once with 1 L water and twice with 1.5 L of methanol at 50° C., and dried.

843.5 g of the crude product was dissolved in 5.5 L of DMA at 55° C., treated with decolorizing charcoal (20 g) and filtered. 1.5 L water was added until crystals began forming. The solution was cooled to 0° C. overnight, and the crystalline product was filtered and washed with a 1:1 mixture of DMA and water (2×500 ml), with water (2×400 ml), and finally with acetone (300 ml). The product was dried in vacuo to yield 3,5-diamino-2,4,6-triiodobenzamide (20) (844.2 g, 79.8% yield from (18)). TLC: single spot with an Rf of 0.46 on silica with 90 CHCl$_3$/10 methanol.

C. N-acetyl 3,5-bis-diacetylamino-2,4,6-triiodobenzamide (21)

At room temperature, concentrated sulfuric acid (22.6 ml, 1% by volume) was added over 0.5 hour with vigorous stirring to a slurry of 3,5-diamino-2,4,6-triiodobenzamide (20) (599.72 g, 1.13 moles) in acetic anhydride (2.26 L), and the reaction was heated at 90° C. for 10 hours.

The reaction mixture was slowly poured into 4 times its volume of water. The precipitate was filtered, washed with 800 ml cold water, and dried to yield N-acetyl 3,5-bis-diacetylamino-2,4,6-triiodobenzamide (21) (788.6 g, 94.4% yield). TLC: Rf of 0.63 on silica with 90 chloroform/10 ethanol. Greater than 98% pure with a retention time of 3.5 minutes. Column: Merck LiChrosorb CN (5u). Solvent system: 85 cyclohexane/9 tetrahydrofuran/3 methanol/3 isobutanol. Flow rate: 2 ml/min. NMR: singlet at 2.35 ppm (15H), singlet at 9.00 ppm (lH) in CDCl$_3$. MP: 232°-234° C. (d). Elemental analysis: found:27.67% C, 2.25% H, 5.66% N, 51.27% I; expected:27.60% C, 2.17% H, 5.68% N, 51.66% I, 12.99%O. UV: $\lambda_{max}$=240.1 nm, $\epsilon$=31,156 L/mole.cm.

D. N,N',N''-tris allyl 3,5-bis-acetylamino-2,4,6-triiodobenzamide (22)

To a solution of N-acetyl 3,5-bis-diacetylamino-2,4,6-triiodobenzamide (21) (184.75 g, 250 mMole) in DMA (500 ml) at 0° C. was added 60% sodium methoxide (60.7 g) over a 2-hour period. A vacuum of 20 mm Hg was applied for 1 hour. Allyl chloride (122 ml, 1.5 moles, distilled at 45°-46° C.) was added at 0° C. over 30 minutes. The reaction mixture was stirred at room temperature for 8 hours. Fifty ml methanol and sodium methoxide (1 g) were added, and the reaction mixture was stirred for an additional 10 minutes, then poured slowly into a stirred ice-cooled solution of 0.1N HCl (2.5 L). The resulting precipitate was filtered, washed with water (5×400 ml) and dried in vacuo to yield 169.6 g).

Crystallization: 41.30 g was dissolved in boiling dichloromethane (300 ml), the solution was concentrated to 150 ml, hexane (60 ml) was added until crystals began to form, and the solution was set aside at room temperature for 24 hours. The crystals were filtered, washed with 1:1 dichloromethane-hexane (2×10 ml) and dried to yield 32.9 g. With a second crop (4.29 g) the total yield was 90%. TLC: four isomers with Rf's of 0.51, 0.55, 0.57 and 0.61 on silica in 90 chloroform/10 methanol. MP: mixture: 210° C. One isomer (Rf's on silica 0.51) has mp 212°-213° C.; the other isomer (Rf 0.55) has mp 224.5°-226° C. NMR: Doublet at 1.73 ppm (6H), triplet at 3.9 ppm (2H), doublet at 4.2 ppm (4H), multiplet at 5.1 ppm (6H), multiplet at 5.8 ppm (3H), broad singlet at 8.75 ppm (1H) in DMSO-d6.

E. N,N', N''-tris(2',3'-dihydroxypropyl) 3,5-bis-acetylamino-2,4,6-triiodobenzamide (23)

(22) (38.44 g, 52.44 mMole) and potassium acetate (1.03 g, 1049 mMole) were added to a solution of acetone (50 ml) and water (20 ml), followed by addition of t.-butyl hydroperoxide (38.6 ml of a 65% solution, 261 mMole) and osmium tetroxide (1.329 g, 5.24 mMole). After 4 hours at room temperature, the reaction was poured into water (50 ml) and OsO$_4$ and t.-butyl hydroperoxide extracted with ethyl acetate (5×75 ml). 10% aqueous NaHCO$_3$ (6 ml) was added to the aqueous phase, and the solution was desalted with BioRad AG5010X(*) D mixed bed resin (58 cm×3.5 cm ID column, flow rate of 45 ml/min of water). The water was removed from the product to yield N,N',N''-tris-(2',3'-dihydroxypropyl) 3,5-bis-acetylamino-2,4,6triiodobenzamide (23) (40.7 g, 93% yield).

Analytical Data: HPLC: four isomers of (23) with retention times of 14.5 g, 19, 22 and 24 minutes were resolved (Ratio: 23:46:26:5). They were isolated individually and slowly interconverted at room temperature and somewhat faster in boiling water (25cm×10 mm ID Alltech aminopropyl column, 10μ90:10 acetonitrile/water, 10 ml/min). NMR: singlet at 1.85 ppm (6H), multiplet at 3.6 ppm (15H), broad singlet at 4.5 ppm (6H), triplet at 8.6 ppm (1H), in DMSO-d6. Elemental analysis (monohydrate): found: 28.17% C, 3.69% H, 4.79% N, 44.54% I. Expected: 28.13% C, 3.52% H, 4.92% N, 44.67% I. UV (monohydrate): $\lambda_{max}$=245.2 nm, $\epsilon$=31,180 1/ mole in water.

EXAMPLE IIIB

A. N,N'-bis-allyl diatrizoic acid (25)

Diatrizoate sodium (24) (635.8 g containing 4.0% water per weight, 0.960 mole, Sterling-Winthrop, Inc.) was dissolved in 660 ml water containing 91.5 g (2.4 moles) sodium hydroxide. 204 ml (2.5 moles) of distilled allyl chloride was added and the reaction mixture refluxed at 50°-55° C. for 3.5 hours, then cooled to room temperature and extracted with dichloromethane (5×200 ml). The aqueous layer was heated to 45° C., stirred and 400 ml of 3N HCl was added. The solid product was cooled to 20° C., filtered and washed with ice-cold water (3×250 ml). The material was dried in vacuo at 90° C. Yield of (24) 632.6 g, 95.0%.

B. N,N'-bis-allyl diatrizoic acid chloride (26)

Purified thionyl chloride, (380 ml) was added to N,N'-bis-allyl diatrizoic acid (25) (261.2 g, 376.4 mMole) and the suspension heated under reflux with stirring for 1.3 hours. The solution was cooled to room temperature, and the thionyl chloride was distilled off under vacuum at 20°-25° C., and any traces removed by drying in vacuo over KOH to obtain an off-white amorphous powder (261.42 g, yield 97.5%). MP: 232°-234° C. (dec.).

C. N,N',N''-tris-allyl 3,5-bis-acetylamino-2,4,6-triiodobenzamide (22)

N,N'-bis-allyl diatrizoic acid chloride (26) (1.50 g, 2.11 mMoles) was suspended in dichloromethane (10 ml), and distilled allylamine (552 μl, 7 mMole) added slowly at 40° C. with stirring for 40 min. The reaction mixture was washed with water (1×10 ml), 0.1N HCl (2×10 ml), water (1×10 ml) and then dried (MgSO$_4$). Solvent removal gave an off-white residue (1.55 g)

which was crystallized from dichloromethane-hexane (1.3 g), yield 84%. MP: 207°-208° C. (dec.).

D. N,N'-N'''-tris(2',3'-dihydroxypropyl) 3,5-bis-acetylamino-2,4,6-triiodobenzamide (23)

A suspension of N,N',N''-tris-allyl 3,5-bis-acetylamino-2,4,6-triiodobenzamide (22) (3.2 g, 4.37 mMoles), potassium acetate (0.086 g, 0.87 mMoles), t.-butyl hydroperoxide (2.58 ml of a 65% solution in water, 17.48 mMoles), osmium tetroxide (0.111 g, 0.437 mMoles), acetone (27 ml) and water (5 ml) was stirred at room temperature for 6 hours. The reaction mixture was diluted with 50 ml water and extracted with ethyl acetate (50 ml × 3).

The aqueous layer was desalted on a BioRad AG-501 mixed bed column, and the water evaporated to give N,N',N''-tris-(2',3'-dihydroxypropyl) 3,5-bis-acetylamino-2,4,6-triiodobenzamide (22), (yield: 95%). (Identical to compound (22) from Example IIIA).

EXAMPLE IIIC

A. 3,5-bis-diacetylamino-2,4,6-triiodobenzoic acetic mixed anhydride (28)

A mixture of diatrizoic acid (27) (154 g, 0.25 mole), acetic anhydride (500 ml, 0.5 mole) and concentrated sulfuric acid (10 ml) was heated in an oil bath at 85° C., with stirring, for 4 hours. The reaction mixture was cooled, then slowly added, with stirring, to water (1.5 L) containing ice (500 g). The precipitate was collected by suction filtration, washed with water (7×100 ml) and dried in vacuo at 50° C. overnight to obtain the product, 3,5-bis-diacetylamino-2,4,6-triiodobenzoic acetic mixed anhydride (28), as a white solid, 172 g, yield 93%. TLC: Rf 0.5 (CHCl$_3$/MeOH/ACOH:75/20/5). IR: (KBr):1766 cm$^{-1}$ and 1797cm$^{-1}$ (anhydride carbonyls), 1710$^{-1}$ (acetyl carbonyls) MP: 196 (dec.).

B. 3,5-bis-diacetylamino-2,4,6-triiodobenzoyl chloride (29)

A suspension of the anhydride (28) (171 g, 0.24 mole) in thionyl chloride (300 ml) was refluxed with mechanical stirring in an oil bath at 80° C. for 1.5 hours. The excess thionyl chloride was removed in vacuo (20 mm of Hg), and the residue coevaporated with ethyl acetate (4×60 ml), and dried in vacuo overnight to obtain 3,5-bis-diacetylamino-2,4,6-triiodobenzoyl chloride (29) (170 g, quantitative yield). TLC: Rf 0.5 (carbon tetrachloride/acetone: 8/2). MP: 231°-232° C. IR: (KBr): 1763cm$^{-1}$ (acid chloride carbonyl), 1710 cm$^{-1}$ (acetyl carbonyls).

C. N-(2',3'-dihydroxypropyl) 3,5-bis-acetylamino2,4,6-triiodobenzamide (30)

2,3-Dihydroxypropylamine (12.10 g, 0.0133 mole) in DMA (10 ml) was added to an ice-cold solution of 3,5-bis-diacetylamino-2,4,6-triiodobenzoyl chloride (29) (35.83 g, 0.05 mole) in DMA (50 ml), with stirring, for 10 min. The reaction mixture was stirred at room temperature, and let stir for 5 hours. Concentrated ammonium hydroxide (30 ml) was added. After 30 min, all solvents were removed in vacuo at 60° C. To the residue, 1N hydrochloric acid (50 ml) was added and the solvent removed in vacuo. The residue was mixed with ice cold water (150 ml) and the precipitate was filtered, washed with water and dried to obtain the product, N-(2',3'-dihydroxypropyl) 2,5-bis-acetylamino-2,4,6-triiodobenzamide (30), as a white solid in high yield.

TLC: (silica gel): 0.36 in CHCl$_3$/MeOH 8:2. NMR: (DMSO-d$_6$): COCH$_3$ (2.02, singlet, 6H); (—CH$_2$— and —CH protons (3.05 to 3.85, broad multiplet, 5H); —OH (4.2, singlet); ArCOHN-(8.4 to 8.7, broad triplet, 1H); Ar—NHCO— (9.85 to 10.15, broad doublet, 2H).

D. N,N'-N''-tris-(2',3'-dihydroxypropyl) 2,4,6-triiodobenzamide (22)

N-(2',3'-dihydroxypropyl) 3,5-bis-acetylamino-2,4,6-triiodobenzamide (30) (136 mg, 0.2 mMole) was heated with sodium bicarbonate (336 mg, 4 mMole) and epichlorohydrin (1 ml, 13.3 mMole) in 1,2-propanediol (2 ml) and a trace of water at 85° C. for 1 hour, to give N, N'-N''-tris-(2', 3'-dihydroxypropyl) 3,5-bis-acetylamino-2,4,6-triiodobenzamide (Example IIIB (23)) in 96% yield by HPLC. HPLC: acetonitrile:water 90:10, 2 ml/m, NH$_2$propyl, 0.5×25 cm, 10µ Alltech column.

EXAMPLE IIID

A. N-(2',3'-dihydroxypropyl) 3,5-bis-(N'-allyl N'-acetyl amino)-2,4,6-triiodobenzamide (31)

N,N'-bis-allyl-diatrizoic acid chloride (26) (see Example IIIA for preparation) (142.6 g, 200 mMole) was suspended in dry DMA (200 ml). 3-Amino-1,2-propanediol (35 ml, 2.25 eq.) was added over 20 minutes with stirring and cooling to keep the temperature of the reaction mixture at 60° C., then stirred at 60° C. for an additional 30 minutes. TLC (90 HCCl$_3$/10 MeOH) indicated 90% conversion to a single product, Rf 0.3. The mixture was poured slowly into stirred ice-water (2 L); the resulting solid was filtered, washed twice with 100 ml ice-cold water and dried in vacuo at 60° C. MP: 220°-221° C. (dec.).

B. N,N',N''-tris-(2',3'-dihydroxypropyl) 3,5-bis-acetylamino-2,4,6-triiodobenzamide (23)

Osmium tetroxide (12 ul of a 0.79M solution, 0.95 µMole) and t.-butyl hydroperoxide (73 µl of a 65% solution, 47 µMole) were added to a suspension of N-(2', 3'-dihydroxypropyl) 3,5-bis-(N'-allyl N'-acetyl amino)-2,4,6-triiodobenzamide (31) (72.4 mg, 9.4 µMole), potassium acetate (5.0 mg) in acetone (900 µl), and water (50 µl) and the reaction allowed to proceed at room temperature for 4 hours to yield N,N',N''-tris-(2',3'-dihydroxypropyl) 3,5-bis-acetylamino-2,4,6-triiodobenzamide (23), identical to product (23) from Example IIIA (yield 90%).

EXAMPLE IV

A. N-(1',3'-dihydroxyprop-2-yl) 3,5-bis-(N'-allyl, N'-acetyl amino)-2,4,6-triiodobenzamide (32)

N,N'-bis-allyl diatrizoic acid chloride (26) (see Example IIIB) (35.6 g, 50 mMole) was suspended in a stirred, dry DMA solution (63 ml). To this solution was added 2-amino-1,3-propanediol, 4.1M in DMA (37 ml, 3.0 eq.) over a 10 minute period and the reaction mixture stirred for 1.5 hours. The mixture was poured slowly into stirred, ice-cooled water (1:1), the resulting solid was filtered, washed twice with 50 ml of ice-cooled water, and dried in vacuo. TLC: Two isomers with Rf's of 0.33 and 0.37 in chloroform 9:methanol 1. TLC indicated quantitative conversion to (32). MP: 240°-243° C. (dec.). UV: λmax=245.2 nm, ε=33,950 l/mole cm. NMR: (DMSO-d6) 1.85-1.60 (d, 6H), 3.9-3.4 (M, 5H), 4.25-4.05 (d, 4H), 6.1-5.4 (M, 2H), 8.6-8.4 (d, 1H). Elemental analysis: Calculated: 31.31%C, 3.15%H, 5.48%N, 49.63%I; Found: 30.99%C, 3.31%H, 5.32%N, 49.00%I.

B. N-(1',3'-dihydroxyprop-2-yl) 3,5-bis-(N'-acetyl, N'-(2'',3''-dihydroxypropyl) amino)-2,4,6-triiodobenzamide (33)

A suspension of N-(1,3-dihydroxyprop-2-yl) 3,5-bis-(N'-allyl, N'-acetyl amino)-2,4,6-triiodobenzamide (32) (3.83 g, 5.0 mMole), potassium acetate (0.99 g, 1.0 mMole) t.-butyl hydroperoxide (3 ml of a 65% solution in water, 20.4 mMole), osmium tetroxide (0.635 ml of a 0.787M solution in acetone, 0.5 mMole), acetone (8 ml) and water (2 ml) was stirred at room temperature for 5 hours. The mixture was then diluted with 10 ml of water and washed with ethyl acetate (6×10 ml).

The aqueous solution was passed through a BioRad AG-501-X8(D) mixed bed column, and the water evaporated. Drying under vacuum (1.0 mm Hg) at room temperature for 1 hour gave the product N-(1',3'-dihydroxyprop-2-yl) 3,5-bis-(N'-acetyl, N'-(2'',3''-dihydroxypropyl) amino)-2,4,6-triiodobenzamide (33) (in quantitative yield). Elemental analysis: Calculated: 28.76%C, 3.38%H, 5.03%N, 45.59%I; Found: 28.43%C, 3.40%H, 4.91%N, 44.21%I. NMR: (DMSO-d6) 8.64–8.2 (m, 1H), 4.8–4.35 (m, 6H) disappears after addition of $CF_3CO_2D$, 4.1–3.0 (m, 15H), 1.9–1.6 (d, 6H). UV: $\lambda max=245.4$ nm, $\epsilon=31,900$ l/mole.cm. TLC: Two isomers with Rf's of 0.47 and 0.56 in n-butanol 6.5N acetic acid 4.

EXAMPLE V

A. N,N'-bis-(3,5-bis-(N''-allyl, N''-acetyl amino)-2,4,6-triiodobenzoyl) ethylenediamine (34)

To a stirred suspension of N,N'-bis-allyldiatrizoic acid chloride (26) (see Example IIIB) (5.11 g, 7.0 mMole) in DMA (70 ml), distilled ethylenediamine (0.5 ml, 15 mMole) was added at room temperature. After 8 hours it was filtered through Celite. Solvents were distilled off and the residue dissolved in a mixture of THF (150 ml) and ethyl acetate (50 ml). The solution was washed with a mixture of brine and 1N HCl (1:1) (1×50 ml), water (2×50 ml), and with brine (1×50 ml). 20 The organic layer was dried (MgSO4) Filtration, followed by removal of the solvent, yielded the product as an off-white solid (3.29, yield 66.6%).

B. N,N'-bis-(3,5-bis-(N''-(2',3'-dihydroxypropyl), N'''-acetyl amino)-2,4,6-triiodobenzoyl) ethylenediamine (35)

Osmium tetroxide (54 mg, 0.21 mMole) was added to a suspension of N,N'-bis-(3,5-bis-(N''-allyl, N''-acetyl amino)-2,4,6-triiodobenzoyl) ethylene diamine (34) (3.325 g, 2.15 Mole) in a mixture of water (5 ml), acetone (19 ml) and dioxane (40 ml) containing potassium acetate (45 mg, 0.46 mMole) and t.-butyl hydroperoxide (2.50 ml of a 65% aqueous solution, 17 mMole). The mixture was stirred at 25–30° C. for 17 hours. Acetone and dioxane were evaporated, water (50 ml) was added and the mixture filtered and extracted into ethyl acetate. 10% Aqueous $NaHSO_3$ (2.5 ml) was added to the aqueous phase, the salts were removed on a mixed bed resin (BioRad AG-501-X8-(D)), and the solution was concentrated to yield the product (35) in nearly quantitative yield by TLC, which was purified. TLC: Four isomers with Rf's of 0.44, 0.49, 0.52 and 0.55 on silica gel in 9:1 chloroform:methanol.

EXAMPLE VIA

A. N-(2,3-dihydroxypropyl) ethylenediamine (36)

Following the procedure of Surrey et al., J. Am. Chem. Soc. (1952) 74:4102, 3-chloro-1,2-propanediol (8.36 ml, 0.10 mole) was added dropwise over 15 min to stirring ethylenediamine (66.8 ml, 1.0 mole) at room temperature. After the addition was complete, the solution was heated at approx. 60° C. until the 3-chloro-1,2-propanediol was consumed (about 1 hour), as determined by TLC. NaOH (4.4 g, 0.11 mole) was added to the solution and excess ethylenediamine was vacuum distilled off followed by careful fractional distillation to yield 5.76 g (43%) of (36) (b.p. 162° C./2.0 mm).

B. N-(2',3'-dihydroxypropyl),.N,N'-bis-(3,5-bis-acetylamino-2,4,6-triiodobenzoyl) ethylenediamine (37)

Into a cooled (0°–5° C.) stirred solution of 3,5-bis-diacetylamino-2,4,6-triiodobenzoyl chloride [(29) see Example IIIC] (100.0 g, 0.153 mole) and triethylamine (43 ml, 0.306 mole) in DMA (450 ml), was added dropwise a solution of N-(2,3-dihydroxypropyl) ethylenediamine (36) (12.33 g, 0.92 mole) in DMA (60 ml) over a 30 minute period. The reaction mixture was stirred for 18 hours at room temperature, and then poured into 2.5 L of 0.1N HCl. The precipitate was filtered, washed with water to neutral pH, and vacuum-oven dried, and dissolved in methanol (350 ml) containing sodium methoxide (2.26 g, 0.042 mole), and refluxed for 1.5 hours. The methanol was distilled off, the solid dissolved in water (200 ml), and precipitated with 1.0N HCl, filtered, washed with water (2×100 ml) and vacuum oven dried to yield (37) 22.5 g. TLC: Chloroform 15:methanol4:acetic acid 1. One spot with an Rf of 0.30. TLC indicated 95% conversion NMR: (d6-DMSO) 2.0 (S, 12H), 4.3–2.8 (M, 11H) goes to 9H after addition of $CF_3CO_2H$, 4.9–4.3 (M, 2H) disappears after addition of $CF_3CO_2H$, 9.0–8.4 (br S, IH), 10.3–9.8 (br S, 4H).

C. N-(2',3'-dihydroxypropyl), N,N'-bis-(3,5-bis(N''-allyl, N''-acetyl amino)-2,4,6-triiodobenzoyl) ethylenediamine (38)

A stirred solution of N-(2',3'-dihydroxypropyl) N,N'-bis-(3,5-bis-(N''-allyl, N''-acetyl amino)-2,4,6-triiodobenzoyl) ethylenediamine (37) (25.0 g, 0.019 mole), allyl chloride (12.32 ml, 0.15 mole), water (33 ml), methanol (155 ml) and potassium carbonate (26.1 g, 5.3 mole) was heated to 43° C. for 24 hrs. All solvents were evaporated off and the residue redissolved into 200 ml of DMA, and poured into stirred water (600 ml). A precipitate was washed with water (2×100 ml) and vacuum oven dried to yield (38) 15.8 g (56.6%). TLC: Chloroform 9:methanol 1. Four isomers with Rf's of 0.39, 0.40, 0.43 and 0.45. NMR: (DMSO-d6) 1.75 (S, 12H), 4.5-2.7 (M, 19H), 5.4–4.8 (M, 8H), 6.2–5.4 (M, 4H), 8.3 (S, 1H). TLC: The product appears as four isomers with Rf's of 0.39, 0.40, 0.43 and 0.45 in chloroform 9:methanol 1.

EXAMPLE VIB

A. N-(2',3'-dihydroxypropyl), N,N'-bis-(3,5-bis-(N''-allyl, N''-acetyl amino)-2,4,6-triiodobenzoyl) ethylenediamine (38)

N,N'-bis-allyl diatrizoic acid chloride (26) (42.12 g, 0.059 mole) and triethylamine (16.4 ml, 0.118 mole) was suspended in an ice-cooled, stirred, dry DMA solution (200 ml). To this was added dropwise a solution of N-(2,3-dihydroxypropyl) ethylenediamine (36) (4.76 g, 0.35 mole) in DMA (95 ml) over 15 minutes, and the mixture stirred at room temperature for 48 hours. The mixture was poured slowly into 1L of stirred water to yield a solid product (38) TLC indicated over 95% conversion.

B. N-(2'3'-dihydroxypropyl), N-,N'-bis-(N'',N''-bis-2'',3''-dihydroxypropyl) 3,5-bis-acetylamino-2,4,6-triiodobenzoyl) ethylenediamine (39)

Into a solution of water (6.34 ml), acetone (25.35 ml), potassium acetate (49.87 mg, 0.50 mMole), t.-butyl hydroperoxide (7.51 ml of a 65% solution in t.-butanol, 50.8 mMole) and osmium tetroxide (3.21 ml of a 1 g $OsO_4$ in 50 ml t.-butanol solution, 0.25 mMole) at room temperature, was added to N-(2',3'-dihydroxypropyl) N,N'-bis-(3,5-bis-(N''-allyl, N''-acetyl amino)-2,4,6-triiodobenzoyl) ethylenediamine (38) (9.43 g, 6.34 mMole). After stirring for 22 hours at room temperature, 63 ml of water was added to the reaction mixture, which was extracted with ethyl acetate (3×60 ml). The aqueous layer was evaporated, redissolved in water and desalted by a mixed bed ion exchange resin (AG-501-X8(D)). The solution was evaporated to yield 8.4 g (81.6%) of N-(2', 3'-dihydroxypropyl), N,N'-bis-(N'',N'-bis-(2'',3''-dihydrohydroxypropyl) 3,5-bis-acetylamino-2,4,6-triiodobenzoyl) ethylenediamine (39). NMR: (d6-DMSO) 1.8 (S, 12H), 4.2–2.7 (M, 29H). 5.1–4.2 (br S, 12H) disappears upon addition of $CF_3CO_2H$, 9.1–8.4 (br S, 1H). UV: $\lambda_{max}$=246.0 nm, $\epsilon$=67,280 l/mole.cm.

EXAMPLE VII

A. N-(2'-hydroxyethyl), N,N'-bis-(3,5-bis-acetylamino-2,4,6-triiodobenzoyl) ethylenediamine (40)

Into a cooled (0°–5° C.), stirred solution of 3,5-bis-diacetylamino-2,4,6-triiodobenzoyl chloride (29), (50.0 g, 0.077 mole) and triethylamine (21.4 ml, 0.154 mole) in DMA (182 ml), was added dropwise a solution of N-(2-hydroxyethyl ethylenediamine (4.66 ml, 0.046 mole) in DMA (10 ml) over a 30-minute period. The reaction mixture was stirred at room temperature for 18 hours, then poured into 1.0 L of 0.1N HCl. The precipitate was filtered, washed with water to neutral pH, and vacuum oven dried. The residue was dissolved in methanol (273 ml) containing sodium methoxide (6.51 g. 0.12 mole) and refluxed for 1.5 hours. The methanol was distilled off, the solid dissolved in water (150 ml), and precipitated with 1.0N HCl, filtered, washed with water (2×100 ml) and vacuum oven dried to yield 34.08 g (96.3%, 0.26 mole) of N-(2'-hydroxyethyl), N,N'-bis-(3,5-bis-acetylamino-2,4,6-triiodobenzoyl) ethylene diamine (40). TLC: Chloroform 15:methanol 4:acetic acid 1. Product Rf: 0 39. NMR: (DMSO) 9.95 (br S, 4H), 9.0–8.5 (br S, 1H), 4.0–2.9 (br M, 15H) goes to 8H after addition of $CF_3CO_2H$, 2.05 (S, 12H).

N-(2'-hydroxyethyl), N,N'-bis-(3,5-bis-(N''-allyl, N'' acetyl amino)-2,4,6-triiodobenzoyl) ethylenediamine (41)

A stirred solution of N-(2'-hydroxyethyl) N,N'-bis-(3,5-bis-acetylamino-2,4,6-triiodobenzoyl) ethylenediamine (40) (15.0 g, 0.012 mole), allyl chloride (10.68 ml, 0.13 mole), water (17 ml), methanol (83 ml) and potassium carbonate (12.46 g, 0.09 mole) was heated at 43° C. for 24 hrs. All solvents were distilled off, the remaining solid filtered, washed with water and vacuum oven dried to yield 12.95 g (76.9% isolated yield) of N-(2'-hydroxyethyl), N,N'-bis-(3,5-bis-(N''-allyl, N''-acetyl amino)-2,4,6-triiodobenzoyl) ethylenediamine (41). TLC: Chloroform 9:methanol 1. TLC indicated substantially quantitative yield. The product gives four isomers with Rf's of 0.52, 0.56, 0.60 and 0.65. NMR: (DMSO-d6) 1.75 (S, 12H), 4.5–2.7 (M, 40H) goes to 16H after addition of $CF_cCO_2H$, 5.4–4.8 (M, 8H), 5.4–4.7 (M, 8H), 6.2–5.45 (M, 4H), 9.1–8.4 (br M, 1H).

C. N-(2'-hydroxyethyl) N,N'-bis-(3,5-bis-(N'''-2'',3''-dihydroxypropyl, N'''-acetyl amino)-2,4,6-triiodobenzoyl) ethylenediamine (42)

A suspension of N-(2'-hydroxyethyl), N,N'-bis-3,5-bis-(N''-allyl, N''-acetyl amino)-2,4,6-triiodobenzoyl) ethylenediamine (41) (12.0 g, 8.24 mMole), potassium acetate (0.065 g, 0.66 mMole), t-butyl hydroperoxide (9.72 ml of a 65% solution in water, 65.9 mMole), osmium tetroxide (4.19 ml of a 0.0787M solution in t-butanol, 0.33 mMole), acetone (33 ml) and water (8.2 ml) was stirred at room temperature for 26 hrs, was diluted with 80 ml of water, and washed with ethyl acetate (3×76 ml).

The resulting aqueous solution was passed through a BioRad AG-501-X8(D) mixed bed column, and the water evaporated. The residue was dried under vacuum (1.0 mm Hg, RT) for 1 hr, yielding 11.08 g (6.96 mMole, 84.5%) of crude N-(2'-hydroxyethyl), N,N'-bis-(3,5-bis-(N-2'',3''-dihydroxypropyl, N''-acetyl amino)-2,4,6-triiodobenzoyl) ethylenediamine (42). NMR: (DMSO-d6) 1.75 (S, 12H), 5.0–2.7 (M, 39H) goes to 28H with the addition of $CF_3CO_2H$, 9.1–8.6 (br S, 1H).

The above procedures describe novel efficient and flexible synthetic strategies which allow for the production of inexpensive non-ionic contrast media in high yield and purity. The method provides for selective substitution of nitrogens depending upon whether they are benzamide nitrogens or aniline nitrogens, where peracylation can be achieved with inexpensive reagents and acyl groups removed selectively to allow for selective nitrogen substitution.

Although the foregoing invention has been described in some detail by way of illustration and example for purposes of clarity of understanding, it will be obvious that certain changes and modifications may be practiced within the scope of the appended claims.

What is claimed is:

1. A method for preparing Iohexol, comprising:
    acylating 5-amino-2,4,6-triiodoisophthaldiamide with acetic anhydride and removing any second acetyl group on a single nitrogen to provide a N, N'N''-triacetyl derivative having the formula;

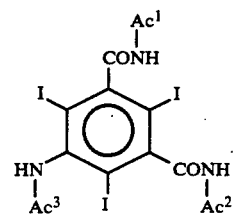

wherein $Ac^1$, $Ac^2$ and $Ac^3$ are each an acetyl group;
    allylating said triacetyl derivative with allyl chloride or allylamine in the presence of base to provide a N, N'N''-triallyl derivative having the formula;

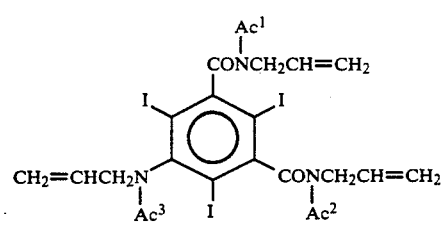

oxidizing olefinic groups of said triallyl derivative introduced by said allylating step to glycols to provide a tris-glycol derivative having the formula;

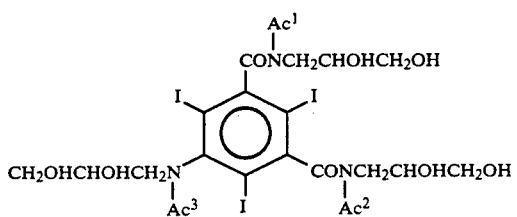

and, removing Ac¹ and Ac² by hydrolysis to produce Iohexol.

2. A method for producing allylated nitrogen atoms of a 2,4,6-triiodobenzamide, comprising:

(i) acylating the nitrogen atoms of a compound of the formula (I)

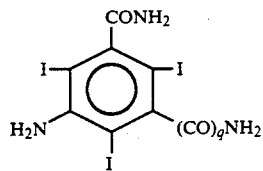

wherein q is 0 or 1, to form a compound of the formula (II)

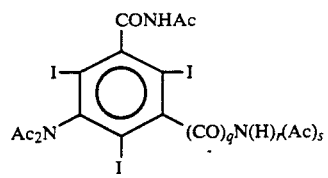

wherein Ac is an acetyl group and r and s are each 1 when q is 1, and r is 0 and s is 2 when q is 0; and (ii) allylating the nitrogen atoms with allyl halide or allylamine under basic conditions to form a compound of the formula (III)

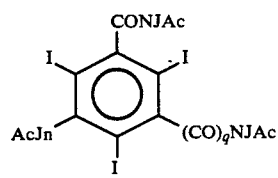

wherein J is allyl,

3. A method according to claim 2, wherein said allylating is with allylamine.

4. A method according to claim 2, wherein said triiodobenzamide is 5-amino-2,4,6-triiodoisophthaldiamide.

5. A method according to claim 4, and also comprising the steps of removing acetyl groups, and oxidizing olefinic groups introduced by said allylating step to thereby provide a compound of the formula (IV)

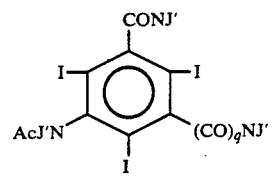

wherein J' is a 2,3-dihydroxypropyl group.

6. A method according to claim 2, wherein said allylating is with allyl halide.

7. A method according to claim 6, wherein said allyl halide is allyl chloride.

* * * * *

UNITED STATES PATENT AND TRADEMARK OFFICE
CERTIFICATE OF CORRECTION

PATENT NO. : 5,191,119
DATED : March 2, 1993
INVENTOR(S) : Milos Sovak et al

It is certified that error appears in the above-indentified patent and that said Letters Patent is hereby corrected as shown below:

Title page, Item [63] please delete "Oct. 7," and insert in lieu thereof --Oct. 17,--.

Item [63] please delete "554,308," and insert in lieu thereof --544,308,--.

Item [56] please delete "Woodward" and insert in lieu thereof --Woodard--.

In column 3, line 27, please delete "$((AQ_2N)_n$" and insert in lieu thereof --$((AW_2N)_n$--.

In column 5, line 28, please delete "alkylati,ng" and insert in lieu thereof --alkylating--.

In column 13, line 14, please delete "t.-butyl" and insert --$\underline{t}$-butyl--.

In column 14, line 18, please delete "in vacuo" and insert --$\underline{in}$ $\underline{vacuo}$--.

In column 14, line 32, please delete "in vacuo" and insert --$\underline{in}$ $\underline{vacuo}$--.

In column 14, line 50, please delete "in vacuo" and insert --$\underline{in}$ $\underline{vacuo}$--.

UNITED STATES PATENT AND TRADEMARK OFFICE
CERTIFICATE OF CORRECTION

PATENT NO. : 5,191,119
DATED : March 2, 1993
INVENTOR(S) : Milos Sovak et al

It is certified that error appears in the above-indentified patent and that said Letters Patent is hereby corrected as shown below:

In column 16, line 12, please delete "t.-butyl" and insert --t-butyl--.

In column 16, lines 19 and 20, please delete "in vacuo" and insert --in vacuo--.

In column 26, line 35, please delete "CONJ'" and insert --CONHJ'--.

In column 26, line 42, please delete "I" and insert --J--.

Signed and Sealed this

Twelfth Day of April, 1994

Attest:

BRUCE LEHMAN

Attesting Officer

Commissioner of Patents and Trademarks